United States Patent [19]

Rothschild et al.

[11] 4,403,939
[45] Sep. 13, 1983

[54] PROCESS AND APPARATUS FOR PRODUCING A MOLECULARLY ORIENTED FILM

[75] Inventors: Kenneth J. Rothschild, Newton, Mass.; Noel A. Clark, Boulder, Colo.

[73] Assignee: Trustees Boston University, Boston, Mass.

[21] Appl. No.: 187,644

[22] Filed: Sep. 16, 1980

Related U.S. Application Data

[62] Division of Ser. No. 13,026, Feb. 21, 1979, Pat. No. 4,241,005.

[51] Int. Cl.$^3$ ............................................. B29C 5/04
[52] U.S. Cl. ..................................... 425/425; 118/50; 118/52; 425/117; 425/434; 425/812
[58] Field of Search .............. 425/425, 117, 434, 812; 233/14 R, 14 A; 118/52, 55, 50; 264/311; 427/240, 241; 494/20

[56] References Cited

U.S. PATENT DOCUMENTS

| | | | |
|---|---|---|---|
| 2,346,784 | 4/1944 | Pollack | 264/311 X |
| 3,036,341 | 5/1962 | Taylor | 264/311 X |
| 3,674,197 | 7/1972 | Mitchell et al. | 233/14 R |

*Primary Examiner*—Evan K. Lawrence
*Attorney, Agent, or Firm*—Paul J. Cook; Lawrence Gilbert

[57] ABSTRACT

Apparatus for forming a film of uniformly oriented molecules from a solution or suspension of the molecules including means to house the molecules in a swinging bucket centrifugation apparatus. The housing means has a gravitational isopotential surface with a radius of curvature equal to the distance between the surface and the spin axis of the centrifugation apparatus. The isopotential surface is normal to the direction of the gravitational forces during spinning. Means for evaporating solvent during centrifugation is provided.

2 Claims, 6 Drawing Figures

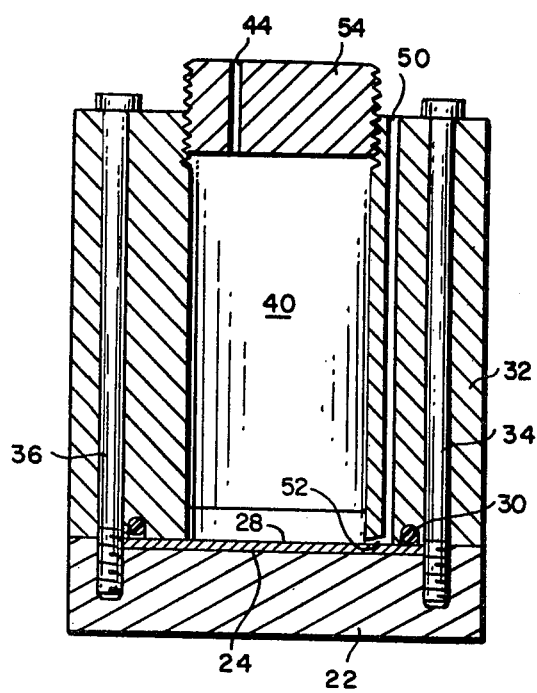
FIG.3
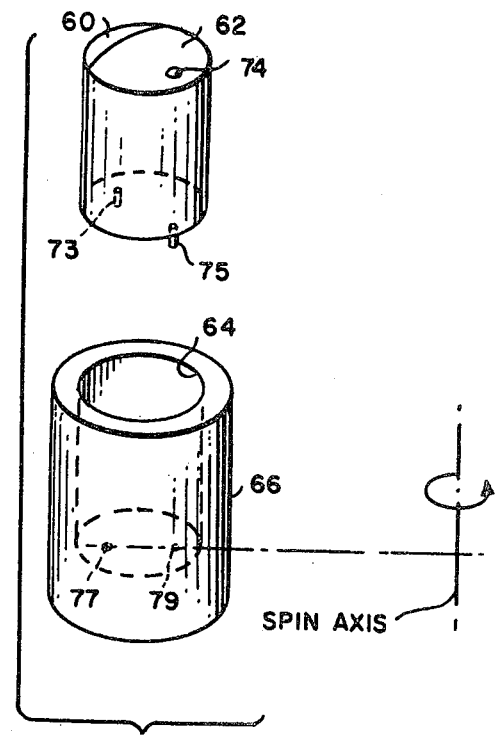
FIG.5
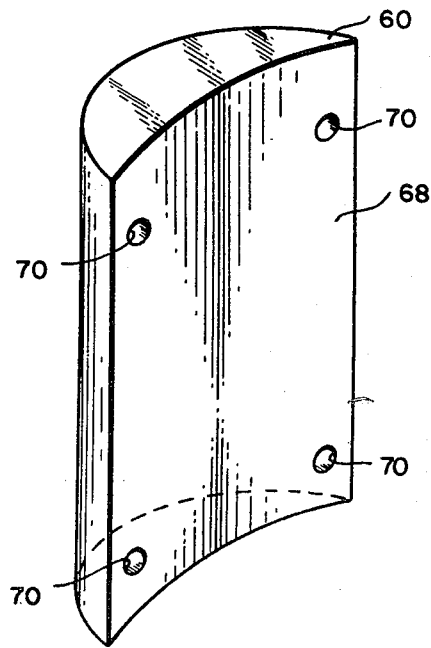
FIG.4
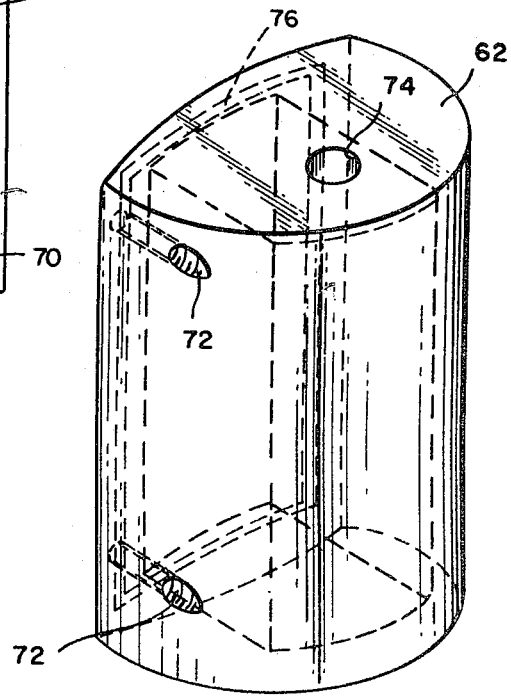

PROCESS AND APPARATUS FOR PRODUCING A MOLECULARLY ORIENTED FILM

This is a division of application Ser. No. 013,026, filed Feb. 21, 1979, new U.S. Pat. No. 4,241,005.

BACKGROUND OF THE INVENTION

This invention relates to a method and apparatus for producing thin films having uniform molecular orientation. More particularly, this invention relates to a method and apparatus for producing such films having a sufficient thickness to permit analysis of their structure by a variety of physical methods.

In order to adequately determine the structure of high molecular weight components of a biological membrane, it is often desirable that the membrane be incorporated into a relatively thick film on the order of at least about 5 microns in thickness and that the high molecular weight components be uniformly oriented. The higher the degrees of orientation, the more structural information can be obtained. Ideally this orientation is three-dimensional such as found in a crystal but can also be two-dimensional or one-dimensional such as found in various types of liquid crystals. In addition, the film must be deposited on a suitable substrate. Films having such a structure then can be analyzed advantageously by presently available techniques including X-ray scattering, visible-UV linear dichroism, polarized infrared absorption, polarized Raman light scattering, Fourier transform infrared spectroscopy, circular dichroism, nuclear magnetic resonance or polarized flourescence spectroscopy. By permitting the use of these and other analyzing techniques, it is possible to provide a precise picture of the structure of the molecular fragments forming the film. Such information would be useful for understanding the functioning of biological membranes from normal and diseased cells. Such information, also, would be useful in the design of films from other molecules such as liquid crystal forming compounds, polymer fragments or from molecular structures such as micelles, vesicles or artificial biological membranes in order to tailor the physical characteristics of the film as desired. For example, it would be desirable to provide thin films having photoconductive characteristics, the ability to selectively transport ions or other substances, light sensitivity or other energy transducing characteristics. It would also be desirable to provide thin films having uniform molecular orientation in order to produce a film which has a specific property, such as increased strength due to orientation or properties which can be utilized in precise analytical techniques. For example, it would be desirable to provide a permeable film having a surface or bulk volume which has a uniform concentration of a specific binding composition such as an enzyme, an antigen or an antibody so that the corresponding substrate, antibody or antigen thereby could be selectively isolated. Examples of other properties of films in which it would be desirable to provide specialized surface or bulk properties include photo-induced reactive films, multilayered films, each layer differing in composition and binding properties, or porous films containing oriented pores, or films with high tensile strength.

Prior to the present invention, a number of techniques have been available to form thin films having essentially uniform molecular orientation. Unfortunately, the films produced in the prior art techniques are too thin to afford their use in a wide variety of testing procedures and/or are not sufficiently molecularly oriented and/or cannot be deposited on the proper substrate. For example, one such technique utilizes a magnetic or electric field to orient the molecules forming the film. Another procedure utilizes hydrodynamic flow wherein the molecules comprising the film are oriented under the influence of a moving liquid stream. Alternatively, it has been proposed to dip a flat substrate repeatedly into an aqueous suspension containing the molecules used to form the film, wherein, after dipping, the aqueous solvent is evaporated prior to re-immersing the substrate into the solution. While all of these procedures yield films having their molecules oriented, the resulting film is too thin or the degree of molecular orientation is insufficient to permit accurate analysis of the molecules forming the film. It has also been proposed to form a film by centrifugation, e.g. J. Mol. Biol. (1975), 93, 123–138, Henderson. In this procedure, a film is spun down from a suspension of the film onto a flat surface within a centrifuge tube in order to form a film oriented well enough to carry out x-ray scattering experiments. While the surface of the film produced is oriented, the thickness of the film is not at all uniform. Furthermore, the orientation is dependent upon the density difference between the film fragments and the solution which can be very small. This phenomenon limits the orientation that can be obtained with this technique.

It would be highly desirable to provide a method and apparatus for forming thin films having uniform molecular orientation of sufficient and uniform thickness to permit their analysis by presently available techniques including x-ray scattering, polarized infrared absorption, UV-visible linear dichroism, or polarized Raman light scattering. Furthermore, it would be desirable to provide such films having uniform surfaces, compositions and properties such as optical properties, specific reactivity, electro-conductivity or electro-chemical properties.

SUMMARY OF THE INVENTION

This invention is based upon the discovery that multilayer films (smectic liquid-crystals) having uniform molecular orientation and having a thickness greater than about $10\mu$ can be formed by centrifugation of a suspension containing membrane fragments onto a curved gravitational isopotential surface while effecting evaporation of the solvent or liquid suspending medium from the membrane suspension. The surface upon which film deposition and formation is initiated has a radius of curvature equal to the distance between the spin axis of the centrifuge and the surface upon which membrane deposition is initiated. The film is produced in the apparatus of this invention comprising a swinging bucket apparatus with means to house the solution or suspension. The housing means has a gravitational isopotential surface with a radius of curvature equal to the distance between the spin axis of the centrifugation apparatus and the isopotential surface. Means are provided for evaporating liquid while the centrifugation apparatus is spinning.

BRIEF DESCRIPTION OF THE DRAWINGS

FIG. 3 is a close-up view of an alternative embodiment of the apparatus of this invention.

FIG. 4 is an exploded view of the apparatus of this invention useful in a fixed rotor.

FIG. 5 shows the apparatus of FIG. 4 positioned in a fixed rotor.

DESCRIPTION OF SPECIFIC EMBODIMENTS

Figure 1:
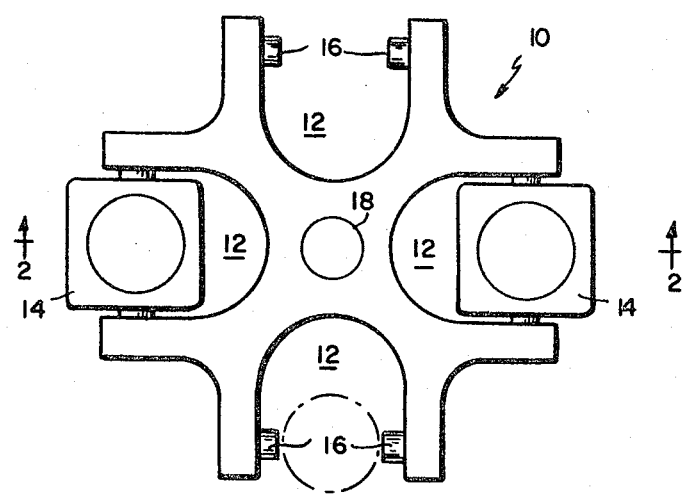
FIG. 1 is a top view of the apparatus of this invention.

Using the apparatus of this invention, a thin film having uniform molecular orientation is formed from a suspension of membrane fragments by centrifuging the suspension onto a gravitational isopotential surface while slowly evaporating the solvent or liquid suspending medium. The gravitational isopotential surface effective within the spinning cavity containing the suspension is any surface whereupon the sum of centrifugal and gravitational forces are everywhere locally normal to the surface. At high rotational speed centrifugal forces dominate and the isopotential surface is cylindrical having the axis of rotation as its axis and to a high degree of approximation a radius equal to the distance of the isopotential surface from the spin axis of the centrifuge apparatus. Hence, the centrifugal forces generated during high speed centrifugation are perpendicular at all points to the isopotential surface.

As noted above, the liquid solvent or suspending medium is evaporated during centrifugation. As evaporation of the solvating or suspending liquid proceeds, the solvated or suspended molecules or molecular structures are compressed between the effective gravitational isopotential bottom surface and the liquid surface, also a gravitational isopotential surface. At high rotational speed the isopotential liquid surface evaporates to provide an effective means of orienting the suspended or solvated molecules or molecular structures. The actual orientation of the molecules or larger molecular component within the film will vary depending upon the shape and type of molecular or molecular compositions utilized to form the film. In any event, for a given type of membrane fragment suspension or other membrane component, the resultant film will have its molecules uniformly oriented.

Evaporation is conveniently effected by forming a vacuum surrounding the sample cavity and utilizing a plug for the cavity that has a small opening to provide access to the vacuum from the interior of the cavity. The size of the access to the vacuum is small, usually of a diameter between about 10–50$\mu$ in order to regulate evaporation of the solvent or suspending medium to form a dry or selectively solvated film. If solvent evaporation is effected at too high a rate, the solution will boil and the membrane fragments will precipitate prematurely, thereby effecting a random orientation of the membrane fragments. In an alternative embodiment which is particularly useful to prevent accumulation of ionic components or solutes from a solvent or suspending medium which contains an ionic composition or low weight solute relative to the molecular component being centrifuged (spun-down), the apparatus of this invention can be provided with a conduit which extends between the vacuum and a point above and immediately adjacent the film being formed wherein the solvent or suspending liquid is evaporated so that the ionic composition can be drawn away from the film during film formation. This is particularly desirable since it prevents accumulation of salts or other solutes in the film which would disrupt the desired molecular orientation.

Figure 2:
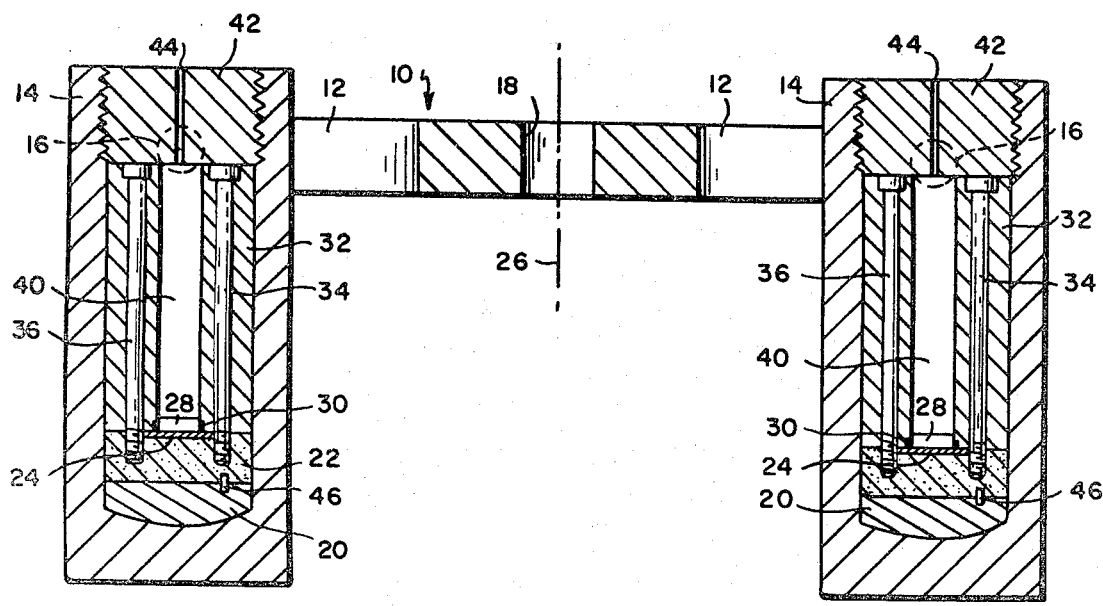
FIG. 2 is a cross-sectional view of the apparatus of FIG. 1 taken along line 2—2.

This invention now will be described with reference to the accompanying drawings. Referring to FIGS. 1 and 2, the centrifuge rotor 10 is provided with a plurality of equally spaced recesses 12 into which are placed buckets 14. The buckets 14 are pivoted on arms 16 which fit into the recesses 12 and into opposing outside surfaces of the buckets 14 in a manner well known in the art. The rotor 10 is provided with a central recess 18 through which a conventional centrifuge spindle is fitted. Each of the buckets 14 contains within its recess a support member 20 and a backing member 22. The upper surface 24 of the backing member 22 is formed to have a radius of curvature equal to the distance of the surface 24 from the spin axis 26 of the centrifuge 10. Thus, when the centrifuge 10 is activated at high speed, the buckets 14 will pivot about arms 16 in a horizontal position and all the points on the surface 24 will be equidistant from the spin axis 26. A substrate 28 upon which the film is formed is positioned above the surface 24 and held thereon by means of O-ring 30 which is positioned below or in a recess on the bottom of cylinder 32. Cylinder 32 is held in place by means of screws 34 and 36 which extend into the backing 22. Useful substrates including glass, quartz, metal foil, polymeric film, ceramics or the like. The substrate 28 can be either flat and made from a relatively flexible material or can be prepared so as to conform with surface 24. For example thin flat glass microscope-cover slips, usually between about 0.02 mm and 1.5 mm thick will conform with a surface 24 of radius 20 cm or greater during centrifugation up to about 20,000 g without fracture. The assembly shown (parts 32, 34, 36, 22, 24), when positioned within buckets 14, can be removed therefrom for filling and unloading to recover the film formed on substrate 24. The O-ring 30 acts to prevent cracking of brittle supporting materials such as glass and to seal the sample chamber 40. The top of the bucket is sealed with a screw cap 42 containing a small, e.g. 10–50 micron hole 44 which functions to allow solvent or liquid suspending medium evaporation into the vacuum chamber (not shown) of a conventional centrifuge compartment. The size of the hole 44 can be varied to alter the rate of evaporation. The nature of the vacuum also can be modified to provide films equilibrated with a specific solvent(s). For example films with varying degrees of hydration could be produced by varying the partial pressure of water in the centrifuge compartment.

In operation, the substrate surface 28 is positioned adjacent surface 24 and the cylinder 32 is secured to backing 22 by means of screws 34 and 36. The chamber 40 is filled with sample and a screw cap 42 is positioned over the cylinder 32. The alignment pin 46 is permanently imbedded in support 20 and fits within a hole within backing 22 to effect proper alignment of the surface 28 with respect to the spin axis. During centrifugation, the membrane fragments are deposited on substrate 28 while liquid suspending medium or solvent is evaporated into the centrifuge vacuum chamber (not shown) through opening 44. Centrifugation is continued until a film having the desired degree of solvation, e.g. dry, is formed on substrate 28.

During the formation of a film or once a film is formed its chemical environment can be altered to affect desired chemical reactions. For example, polymerization could be initiated by introduction of the appropriate gas in the vacuum chamber.

Referring to FIG. 3, an alternative embodiment of the sample holding means of this invention is shown. As shown in FIG. 3, the sample holding means includes the cylindrical sample cylinder 32, the two screws 34 and 36, the backing member 22, substrate 28, O-ring 30 and the sample chamber 40. In the embodiment shown, an evaporation channel or channels 50 is drilled into the sample cylinder 32 with an opening or openings 52 positioned adjacent to and just above the substrate 28 upon which the film is to be formed. A plug 54 can be press-fit or screwed into the top of chamber 44 to provide a tight fit. The plug 54 is provided with a very small pressure equalization channel 44 so as to permit flow of liquid at a controlled rate through channel 50 during centrifugation. The embodiment shown in FIG. 3 is particularly useful when the liquid suspending medium or solvent contains ionized salts or low molecular weight solutes which otherwise would be concentrated at or near the film being deposited but which can be removed from contact with the film through channel 50 under the influence of the vacuum used in the centrifuge apparatus. The opening 52 or channel 50 can be filled with a semipermeable material such as a porous membrane, glass frit or porous ceramic, which serves to regulate the flow of liquid thereby permitting deposition of a molecularly oriented film on substrate 28.

As shown in FIGS. 4 and 5, this invention is useful in fixed angle rotors as well as a swinging bucket rotor. An isopotential centrifuge assembly comprises two segments 60 and 62 which, when joined, are adapted to fit into a vertical cavity 64 of rotor 66 with alignment pins 73 and 75 fitting into holes 77 and 79. Segment 60 includes an isopotential gravitational surface 68 having a radius of curvature equal to the distance from the spin axis of the centrifuge employed. Segment 60 is provided with threaded holes 70 adapted to mate with screws fitting through holes 72 of segments 62 holding segments 60 and 62 together. When segment 60 and 62 are mated, a cavity is formed. The cavity is provided with a hole 74 for filling which can be plugged after the cavity is filled. The plug utilized has a small hole which connects the cavity with the interior of the centrifuge where vacuum is drawn in order to effect controlled evaporation of the liquid solvent or suspending medium in the cavity during centrifugation.

In operation, the assembly shown in FIGS. 4 and 5 is similar to that of the assembly described with reference to FIGS. 1 through 4. A support material such as a glass cover slip is placed on the isopotential surface 68 and is held in place by fastening segments 60 and 62 together. An O-ring or gasket 76 is embedded on the outer surface or segment 62 to prevent liquid leaking from the cavity. The assembly is inserted into rotor tube 66 (FIG. 5) and a centrifuge cap or plug with a small hole is positioned within fill hole 74 after the cavity is filled. The segments 60 and 62, each are provided with prongs 73 and 75 which fit into holes 77 and 79 in order to properly orient surface 68 in relation to the spin axis of the centrifuge. After centrifugation and evaporation of the liquid solvent or suspending medium, the oriented film is removed with the support from the cavity.

Figure 6:
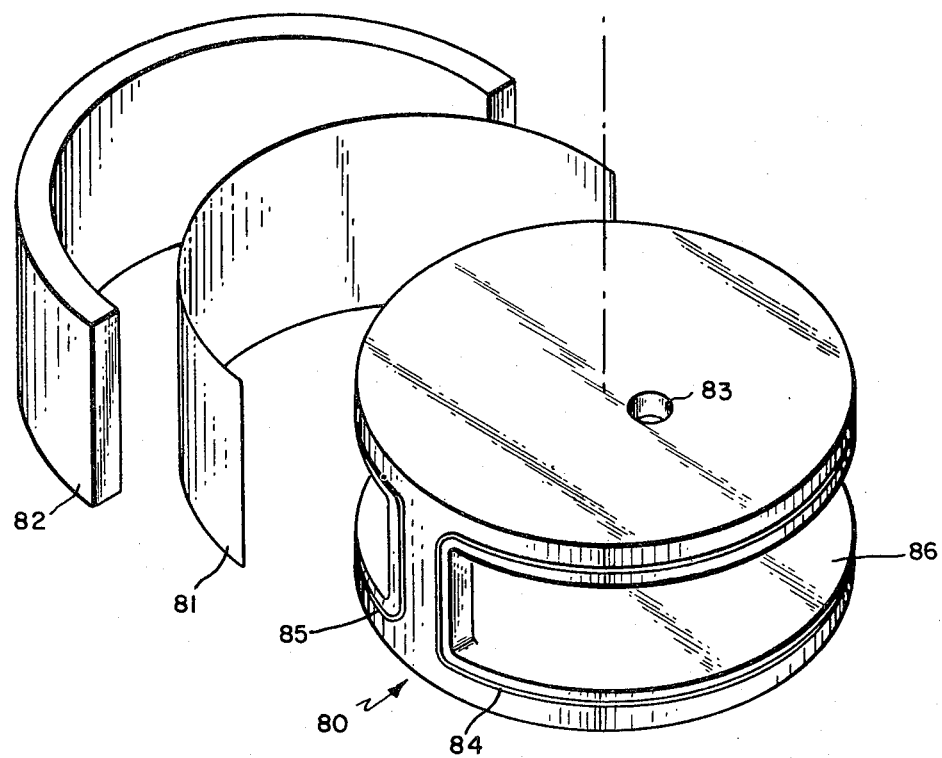
FIG. 6 shows a rotor having an integrated isopotential surface.

As shown in FIG. 6, this invention may be employed using an isopotential surface which is integrated with the rotor body 80. In this case the isopotential substrate surface 81 forms a complete cylinder or nearly complete cylinder. This embodiment is particularly useful when large film areas are required. The isopotential substrate surface 81 is positioned on isopotential backing surface 82. The rotor 80 is provided with a filler hole 83 and suitable O-rings or gaskets 84 and 85. Although not shown, the opening 85 also is closed by an isopotential surface in the manner described above.

The process of this invention is useful to produce a wide variety of molecularly oriented films. For example, polymers, including polyolefins, polyvinyls, acrylinitrile, polypeptides, DNA or the like can be formed in accordance with this invention. In addition, films from naturally occurring sources can be formed such as purple membrane produced from the bacteria, *Halobacterium halobium*, photoreceptor film from rod outer segments, acetocholine receptor, or the like. In one particular aspect of this invention, the membrane fragments can be deposited upon a substrate to which it becomes bound to thereby produce a product having improved mechanical strength over the film which would otherwise be formed and which provides a product having a uniform surface concentration over the entire exposed area. This embodiment is particularly useful when preparing a film composite from materials which function as an antibody or an antigen, an enzyme or a substrate so that the resultant product can be utilized to determine the concentration of an unknown antibody or antigen in a conventional agglutination reaction or an unknown enzyme or substrate in a conventional enzyme-substrate reaction.

The following example illustrates the present invention and is not intended to limit the same.

EXAMPLE I

This example illustrates the process of this invention in the production of a purple membrane having uniform molecular orientation and having a thickness greater than about $10\mu$.

Purple membrane fragments ($0.5\mu$ diameter, 50 Å thick) are isolated from the plasma membrane of bacteria *Halobacterium halobium* using membrane isolation procedures well known in the art. These fragments are suspended in $H_2O$. The suspended solution normally has an optical density at 570 nm of about 0.4 in 1 cm path length cuvette. This corresponds to a concentration of bacteriohodopsin of 10 micromolar. 1 ml of the suspending solution is placed in the sample chamber (40) of an apparatus similar to that shown in FIG. 4. The assembly is designed to fit into the bucket of an SW25.2 Beckman three-bucket swinging bucket rotor. The substrate (28) consists of thin glass coverslips approximately 0.1 mm thickness and $12 \times 12$ mm area or approximately 1 cm diameter discs cut from Mylar, Saran-wrap, aluminum foil, Teflon or other thin sheets. Semipermeable membranes such as available from Millipore Corporation, may also be utilized as substrate. For the case of infrared measurements, AgCl windows are utilized. Three such assemblies with suitable substrates are inserted into the three buckets and the caps (42) screwed in place. The buckets are then mounted on the SW25.2 head and placed in an L350 Beckman ultracentrifuge. The head is centrifuged for approximately 10 hours at 15,000 RPM. The centrifuge compartment is precooled to 5° C. and pumped down to 10 microns pressure. After completion of the spin, the assemblies are removed and the resulting purple membrane film deposited on substrate (28) removed. In the case of many substrate materials such as Saran-wrap, it was found that the substrate could be peeled away from the purple membrane film, resulting in an unsupported film. These films are circular and appear microscopically uniform over the entire area. Based on absorption measurements, the film thickness is approximately 10μ. Thicker or thinner films can be made by adjusting the initial concentration of purple membrane.

Freeze-fracture electron microscopy of purple membrane films reveal they consist of regular lamellar stacks of membranes referred to as the smectic B phase in liquid-crystal terminology. The freeze fracturing technique splits the bilayer in the hydrophobic region of the bilayer resulting in exposed surfaces from the cytoplasmic (c-face) and extracellular (e-face) part of the bilayer. Electron micrographs of freeze-fractured purple membrane films reveal in many areas "step-like" terraces which appear to reflect sheets of membrane layers on top of one another. It has been verified using optical image reconstruction methods that these sheets are produced from the individual purple membrane fragments isolated from the *Halobacterium halobium* plasma membrane. Additional biophysical measurements including IR, UV and visible dichroism indicate the membranes are highly oriented.

This procedure has also been carried out for photoreceptor membrane isolated from the rod outer segments of bovine retinas. We again find results based on analytical measurements which indicate that the photoreceptor membrane orient into regular lamellar stacks. As used in the claims, the term "molecules" is intended to include any precursor to a film such as molecules, polymer fragments, liquid crystal forming compounds or molecular structures such as biological membrane fragments micelles or vesicles or the like.

What we now claim is:

1. Apparatus for forming a film from a suspension or solution of molecules wherein said molecules are uniformly oriented in said film which comprises:
    means to house said molecules adapted to be positioned within a centrifugation apparatus having a spin axis wherein said means is formed integrally into a bucket for a swinging bucket centrifugation apparatus;
    said means having a cavity which includes a gravitational isopotential surface having a radius of curvature equal to the distance of said surface from said spin axis, said isopotential surface being the surface normal to the gravitational forces which are generated when spinning said centrifugation apparatus; and,
    means for evaporating solvent or suspended liquid from said cavity while spinning said centrifugation apparatus.

2. The apparatus of claim 1 wherein said surface is formed into a cavity of a housing adapted to be positioned within a sample cavity of said swinging bucket rotor.

* * * * *